United States Patent [19]
Kraidin et al.

[11] Patent Number: 5,183,051
[45] Date of Patent: Feb. 2, 1993

[54] MEANS AND APPARATUS FOR CONTINUOUSLY DETERMINING CARDIAC OUTPUT IN A SUBJECT

[76] Inventors: Jonathan Kraidin, 3301 Indian Queen La., Philadelphia, Pa. 19129; Irwin Gratz, 411 Woodbine Ave., Penn Valley, Pa. 19072

[21] Appl. No.: 640,968

[22] Filed: Jan. 14, 1991

[51] Int. Cl.⁵ .................................................. A61B 5/02
[52] U.S. Cl. ........................................ 128/687; 128/713; 128/691
[58] Field of Search .............. 128/713, 691, 668, 672, 128/687–689

[56] References Cited

U.S. PATENT DOCUMENTS

| | | | |
|---|---|---|---|
| 3,831,590 | 8/1974 | Boyle et al. | 128/713 |
| 4,429,701 | 2/1984 | Goor et al. | 128/713 |
| 4,834,107 | 5/1989 | Warner | 128/668 |

Primary Examiner—Ruth S. Smith
Assistant Examiner—Robert L. Nasser, Jr.

[57] ABSTRACT

A method for continuously determining cardiac output (CO) in a subject comprising continuously measuring arterial blood pressure data at a site and converting said arterial blood pressure data to a digital signal representative of a pulse contour curve waveform, calculating heart rate, grade of slope, systolic peak pressure, the presence of reflected waves, and pressure at the dicrotic notch from said digital signal; determining the area, SA, under said pulse contour from the start of a pulse to the dicrotic notch of said pulse contour curve; for any pulse which is reflective, subtracting from said area A any portion, B, of said area A, representing an approximate area due to wave reflection to obtain a stroke area, SA; and calculating CO as a product of SA and HR. Apparatus for continuously determining cardiac output (CO) in a subject comprising means for carrying out each step of the method are also disclosed.

21 Claims, 7 Drawing Sheets

MEANS AND APPARATUS FOR CONTINUOUSLY DETERMINING CARDIAC OUTPUT IN A SUBJECT

BACKGROUND OF THE INVENTION

1. Field of the Invention

This invention relates generally to a method for continuously determining cardiac output from a pulse contour curve based on measured arterial pulse data.

2. Description of the Prior Art

The traditional method for continuously determining cardiac output (CO) is the thermodilution method which requires inserting an instrument directly into the body of the patient. There is a safety risk with the thermodilution method and so others have suggested methods for determining CO indirectly from outside the body. Until the present invention, however, none of the non-invasive methods have achieved accuracy close enough to the accuracy of the thermodilution method.

Warner et al, Computer-based monitoring of cardiovascular functions in postoperative patients, Circulation 27 (suppl 2) II 68–74, 1968, suggested computation of cardiac output via computer analysis of the central aortic pulse-wave contour.

Warner U.S. Pat. No. 4,834,107 discloses a non-invasive method for determining heart-related parameters in patients which determines pulse pressure, time constant of the arterial system, systolic and diastolic pressure, peripheral resistance, cardiac output, and mean arterial blood pressure. Warner uses volume data rather than pulse data, and does not recognize the need to adjust for inaccuracies from reflective waves, nor, of course, does Warner describe a method for making the appropriate adjustments. Further, the Warner method apparently must recalibrate for each patient, and does not provide a method for factory calibration while achieving very accurate cardiac output information.

Others have suggested improvements to Warner et al's method; see, for example:

English, et al, Comparison of Aortic Pulse-wave Contour Analysis and Thermodilution Methods of Measuring Cardiac Output during Anesthesia in the Dog, Anesthesiology 52:56–61, 1980;

Wesseling et al, A simple device for the continuous measurement of cardiac output, Adv. Cardiovasc. Phys., 5 (part II):16–52, 1983;

Alicandri et al, Possibility of cardiac output monitoring from the intra-arterial blood pressure profile, Clin. and Exper. Theory and Practice, A7 (2 & 3), 345–353, 1985;

De Meersman, New Noninvasive Computerized Method for the Area Measurement of the Dicrotic Notch, Comput. Biol. Med., 19, No. 3:189–195, 1989;

Wesseling et al, Arterial haemodynamic parameters derived from noninvasively recorded pulsewaves, using parameter estimation, Medical and Biological Engineering, Nov. 1973:724–732; and Stern et al, Anesthesiology, 73, 3A, September 1990, A455, described a new model (pulse contour) for a peripheral arterial waveform analysis describing the fluid and wall motion of the arterial system. The algorithm is described as processing the area under the arterial waveform based on impedance (Zao) along the arterial tree. Stern et al appear to be using the Wesserling et al method, citing "A Simple Device for the Continuous Measurement of Cardiac Output," Adv. Cardiovasc. Phys., vol. 5 (Part II):16–52. Karger, Basel 1983. Stern et al require frequent recalibrations and yet they still only report achieving a correlation of 0.65 and a standard deviation of ±0.8 liters.

In general, the prior methods requires calibration for each patient. In no case is a correction for reflected pulse waves provided.

SUMMARY OF THE INVENTION

It is an object of the present invention to provide a non-invasive method for accurately and continuously determining cardiac output for a subject without having to calibrate for said subject by use of traditional methods.

It is a further object of the invention to provide an apparatus which provides non-invasive or minimally invasive, continuous real time cardiac output information from arterial pulse.

A still further object is to provide a method for continuously determining cardiac output from arterial pulse measurement which corrects for error due to reflected pulse waves.

These objects and others which will become apparent from the following disclosure are achieved by the present invention which comprises in one aspect an apparatus useful for continuously determining cardiac output (CO) in a subject comprising:

means for continuously measuring arterial blood pressure data at a site on said subject;

means for continuously converting said arterial blood pressure data to a digital signal representative of a pulse contour curve waveform;

means for continuously calculating heart rate (HR), grade of slope, systolic peak pressure, the presence of reflected waves, and pressure at the dicrotic notch from said digital signal;

means for determining the area, SA, under said pulse contour curve from the start of a pulse to the dicrotic notch of said pulse contour curve;

for any pulse which is reflective, means for subtracting from said area A any portion, B, of said area A, representing an approximate area due to wave reflection to obtain a stroke area, SA; and means for calculating CO as a product of SA and HR.

In another aspect, the invention is directed to a method for continuously determining cardiac output (CO) in a subject comprising:

continuously measuring arterial blood pressure data at a site on said subject;

continuously converting said arterial blood pressure data to a digital signal representative of a pulse contour curve waveform;

continuously calculating heart rate (HR), grade of slope, systolic peak pressure, the presence of reflected waves, and pressure at the dicrotic notch from said digital signal;

determining the area, SA, under said pulse contour curve from the start of a pulse to the dicrotic notch of said pulse contour curve;

for any pulse which is reflective, subtracting from said area A any portion, B, of said area A, representing an approximate area due to wave reflection to obtain a stroke area, SA; and calculating CO as a product of SA and HR.

BRIEF DESCRIPTION OF THE DRAWINGS

The drawings illustrate but a few of several possible embodiments of the invention.

Other objects and many of the attendant advantages of this invention will be readily appreciated as the same becomes better understood by reference to the following detailed description when considered in connection with the accompanying drawings wherein.

DETAILED DESCRIPTION OF THE INVENTION AND THE PREFERRED EMBODIMENTS

Figure 7:
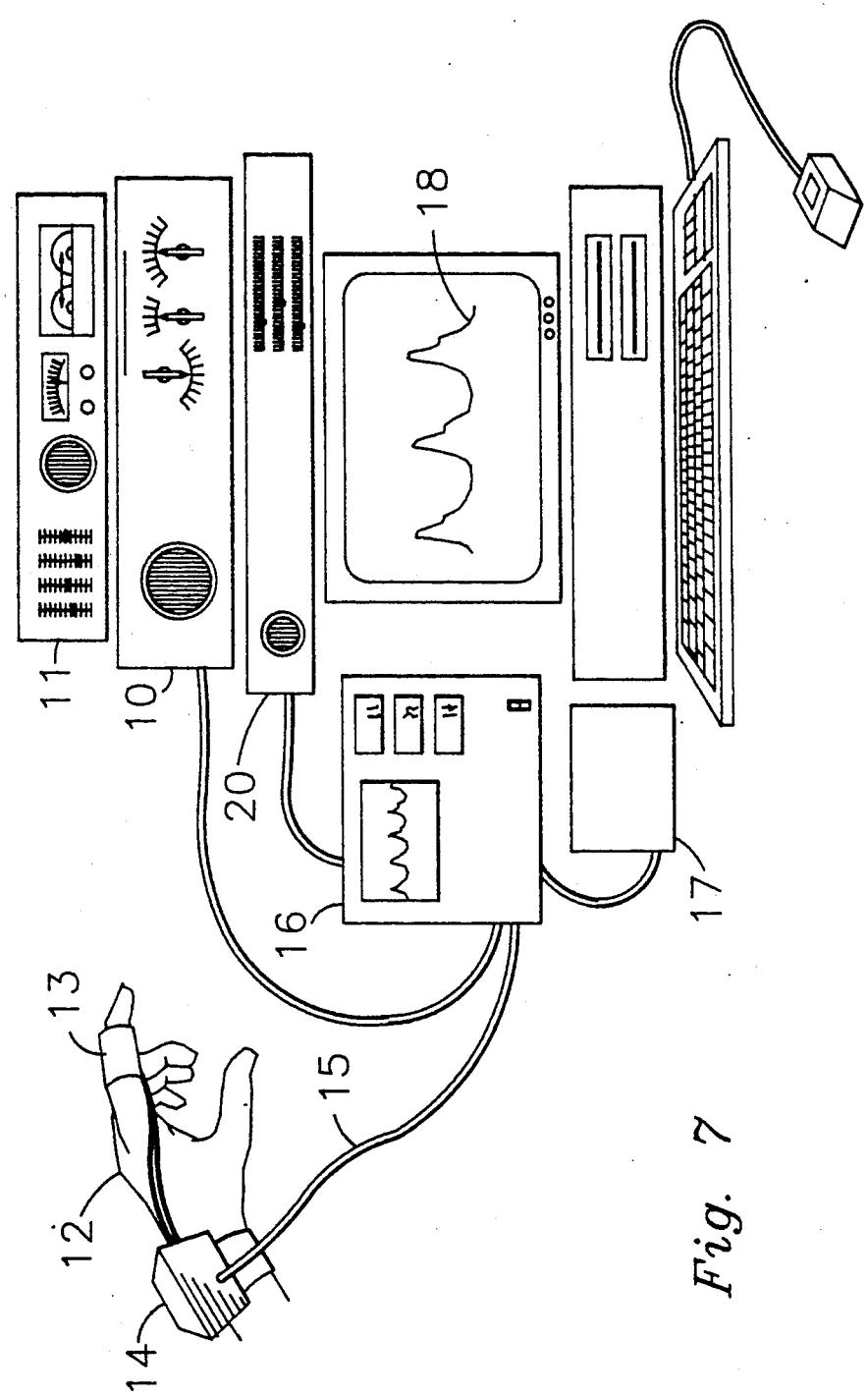
FIG. 7 is a perspective view of a hand of a subject and a front elevational view of the overall apparatus of the invention.

Referring now in greater detail to the various figures of the drawings wherein like reference numerals refer to like parts, in FIG. 7 an apparatus for continuously determining cardiac output (CO) in a subject 12 is illustrated wherein a Finapres® device for continuously measuring variation in arterial blood pressure data at a finger having a finger collar 13, wrist mounted transmission module 14, wire 15, and computer which outputs arterial blood pressure data 16; an analogue to digital converter 17 for continuously converting said arterial blood pressure data to a digital signal representative of a pulse contour curve waveform 18. A computer 19 programmed with an algorithm, described in detail below, functions to continuously calculate cardiac output (CO) from said digital signal with accuracy approaching or matching that of the standard thermodilution method. The apparatus also preferably includes an amplifier 20, a preamplifier 10, and a tape storage device for digital information 11. The apparatus preferably comprises means for continuously calculating for each pulse the portion of the area under the pulse contour curve from where grade of slope equals zero and then increases by a set amount, representing the beginning of a reflected wave, to a point on said curve where said grade of slope exceeds $-60$ mm Hg-sec-1, said point where said grade of slope exceeds $-60$ mm Hg-sec-1 representing the dicrotic notch.

As an alternative embodiment to the non-invasive Finapres device, a minimally invasive arterial line (not shown) for continuously measuring blood pressure at any peripheral site can be used.

It is well known that CO is the product of stroke volume (SV) and heart rate (HR). SV is the volume the heart puts out at each pump. Our method comprises assuming stroke area (SA) under the pulse pressure curve (PPC) between the start of a pulse (upstroke) to the dicrotic notch is proportional to SV. We discovered that while SA is roughly proportional to SV, certain very critical corrections are necessary and we have discovered a method for making such corrections on a continuous basis, and that accurate CO information can be obtained with new patients without ever needing calibration. This information includes the absolute CO and CO trends during an operation, in the intensive care unit, and for outpatients who do not need surgical procedures.

Each patient has a different pulse wave, and within a single patient, there are pulse to pulse variations, not only in frequency, corresponding to HR, and amplitude, corresponding to pulse-pressure, but also variations in shape due to signal distortions and presence or absence of reflective waves and damped waves due to changes in the vascular impedance (VI). These variations are different at different sites of measurement, and are dependant on the patient's vasculature condition. We have discovered that CO can be determined more accurately than previous methods by continuously calculating beat-to-beat the VI. Variations in true CO are due to variations in ventilation, changing hemodynamic conditions and medications administered, and a continuous, correct reading is necessary during surgical procedures to assist the physician in continuous evaluation of these conditions.

Under our method, an algorithm is provided which computes (HR) (also called "pulse period"), grade of slope, systolic peak pressure, diastolic pressure, pulse pressure, mean pressure, diastolic area, the presence of reflected waves, and pressure at the dicrotic notch from said digital signal, and SA. The preferred method is using a decaying exponential expression of the form $Y = A + B^* \exp(-K^* pp)$. Different constants (A, B, k,) are used at different Mean Pressures. An expression for VI can be obtained by fitting a curve to data or generating a theoretical expression. VI is calculated beat-to-beat in the preferred embodiment because VI is never constant.

Figure 1:
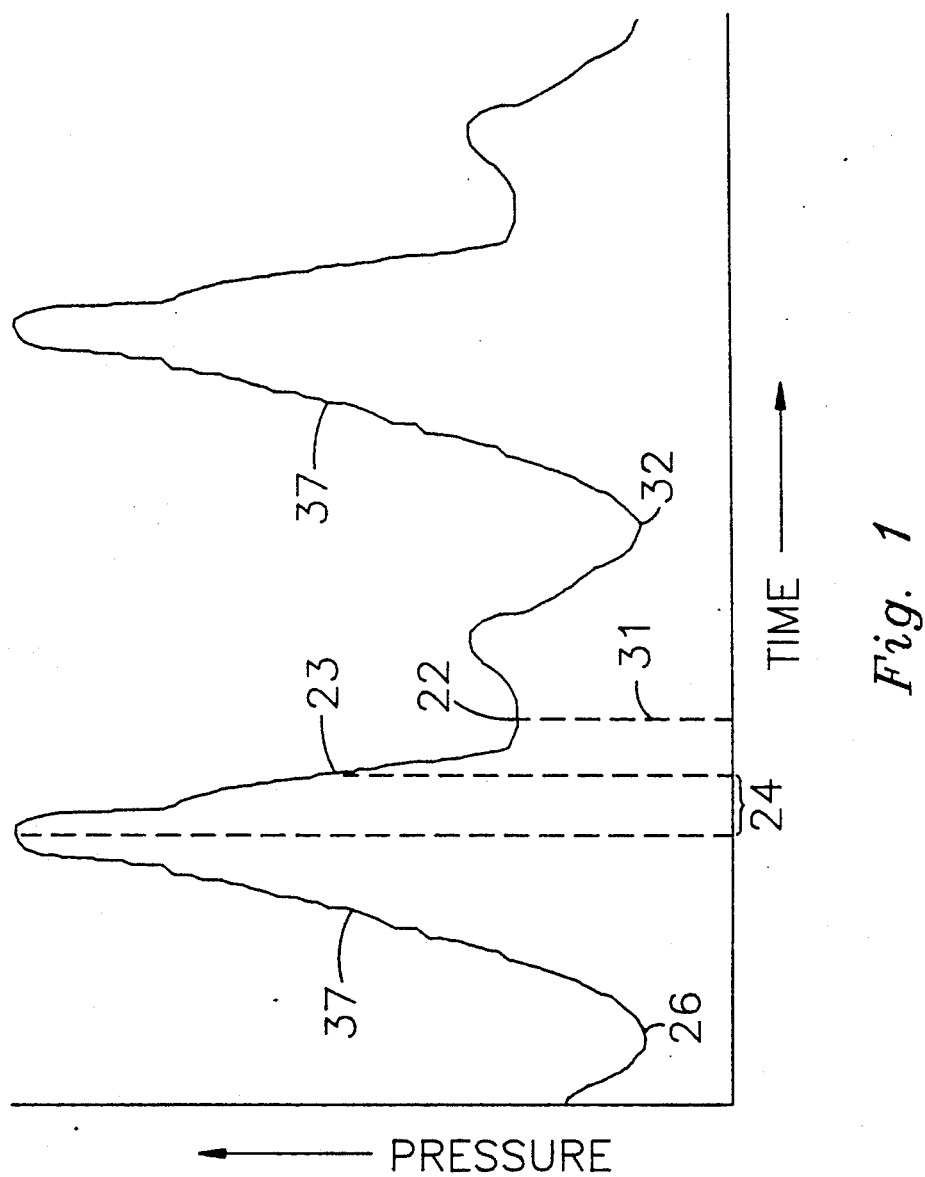
FIG. 1 is normal pulse curve.

More specifically, the algorithm defines a pulse as that portion of a waveform beginning with a sharply rising segment (upstroke), 37 in FIG. 1, which is recognized by the algorithm by its slope exceeding a preset critical value and said value is maintained over a preset period of time. The end 26 or 32 of one pulse denotes the beginning of the next. In order to distinguish the beginning of a pulse from a prominent dicrotic notch, the algorithm determines whether the pulse pressure between the relative minimum and relative maximum exceeds a predefined critical value, preferably 50% of previous pulse pressure. If it does exceed said value, the algorithm identifies the point as the beginning/end of a pulse. The method distinguishes the beginning of a pulse from the end of a prominent dicrotic notch by comparing the slopes and identifying the one with the greater slope to be the upstroke of the pulse. Furthermore, larger pulse pressures have steeper upstrokes and the program also accounts for that in distinguishing upstroke from part of the dicrotic notch.

To determine dicrotic notch, the algorithm uses pulse period as an index into a table of start/end offsets which delimit the boundaries of the dicrotic notch and within these boundaries determines where the instantaneous slope exceeds a critical slope value, then assigns that point 22 as the notch. In cases of a damped curve wherein the curve of the notch does not exceed the critical slope value, the end of the offset is assigned as the location of the notch.

Figure 2:
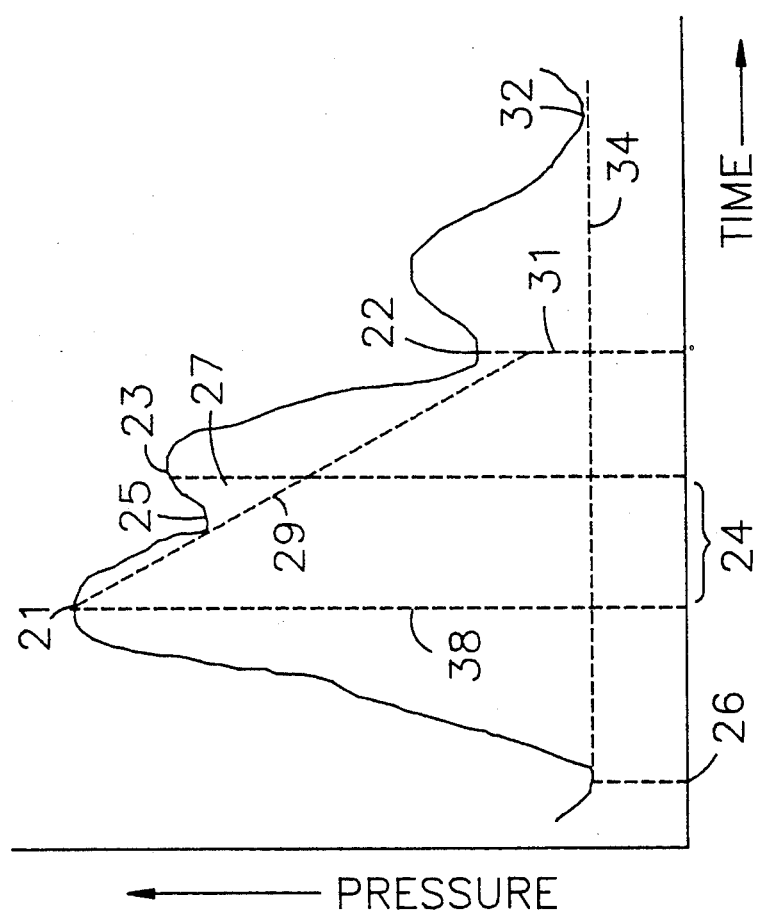
FIG. 2 is a reflective curve showing determination of areas to be subtracted in determining SA.
Figure 3:
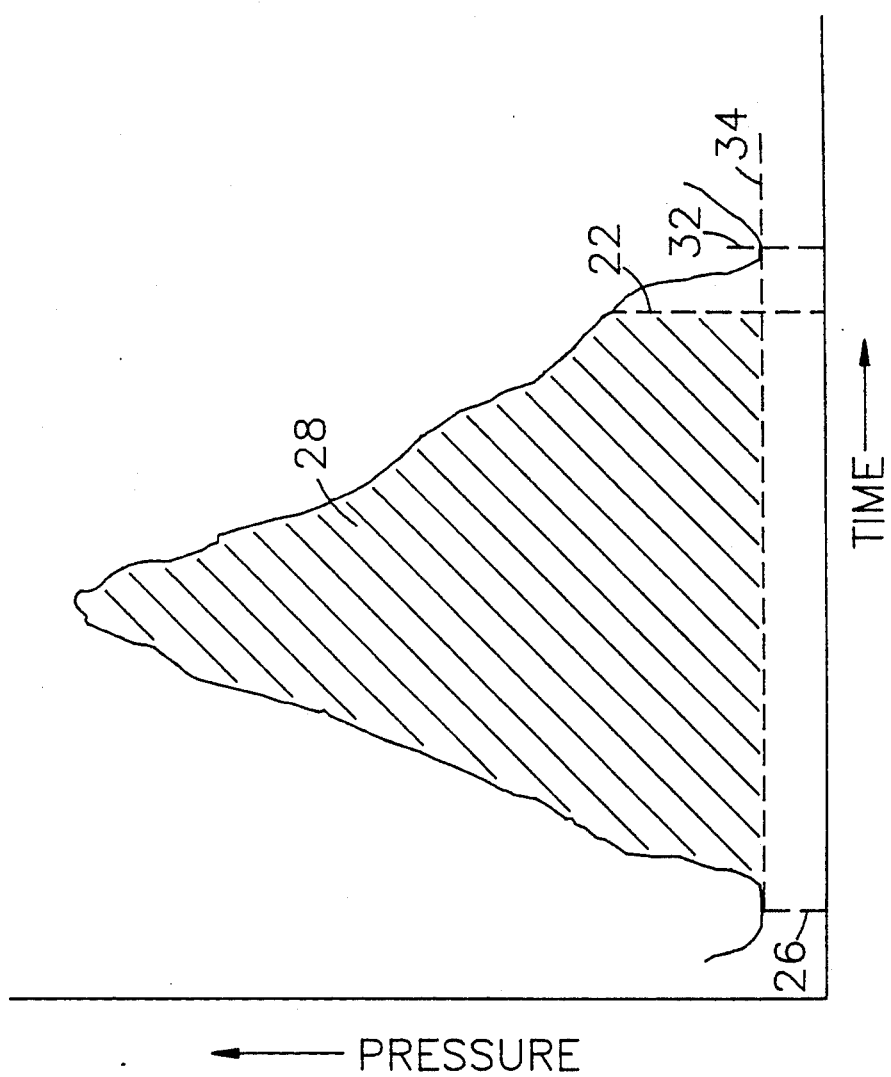
FIG. 3 is a damped curve.

The program handles three different types of pulse wave curves differently: reflective (FIG. 2), normal (FIG. 1), and damped (FIG. 3); and thereby corrects the SA to greatly improve the accuracy of the CO calculation.

A preferred method of determining whether a reflective wave exists is to first find the first apparent systolic peak 21 (FIGS. 1 and 2) where grade of slope is 0, determine the location of the dicrotic notch 22 by conventional steps, divide the distance along the X-axis between the first apparent systolic peak 21 and the dicrotic notch 22 in half to determine search limit 23, and to define a search distance 24 between the first apparent systolic peak 21 and the search limit 23, and then search the search distance 24 for a point 25 where the slope exceeds a critical value and label said point 25 (FIG. 2) as the true systolic peak and the original, apparent systolic peak 21 as a false systolic peak.

Figure 4:
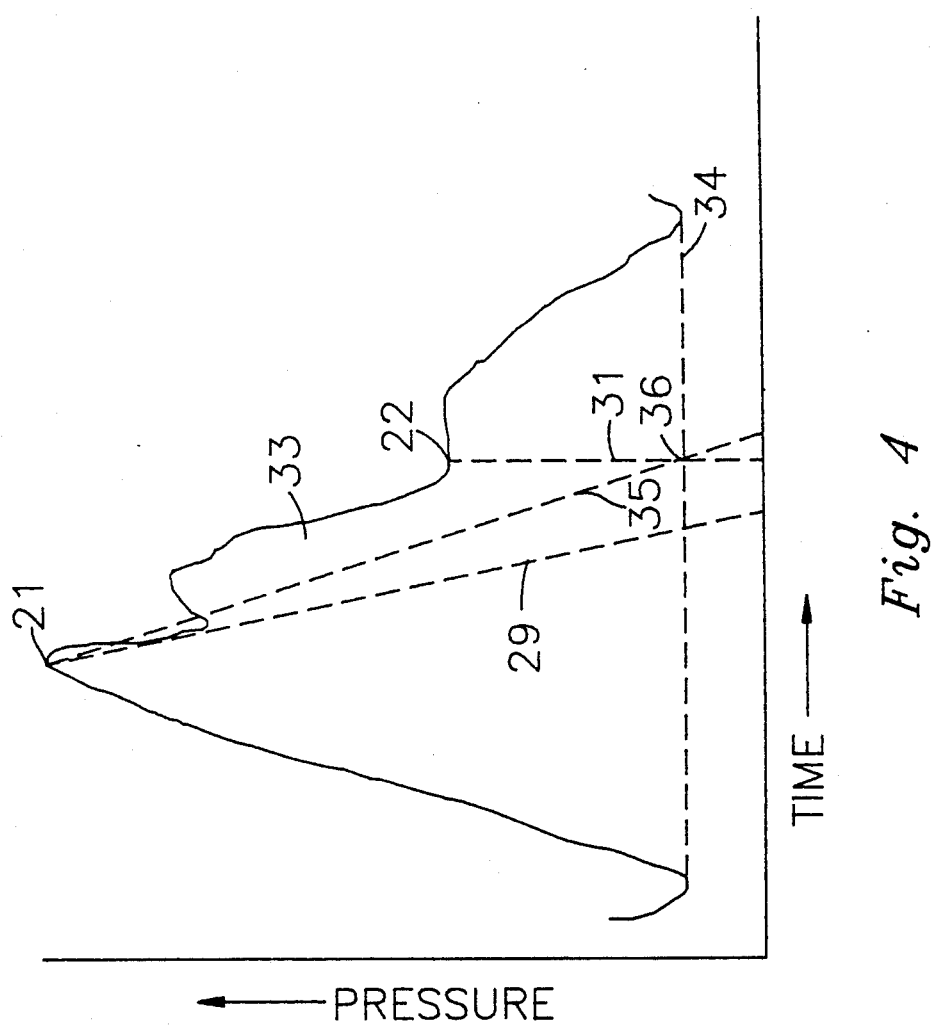
FIG. 4 is a special reflective curve.
Figure 5:
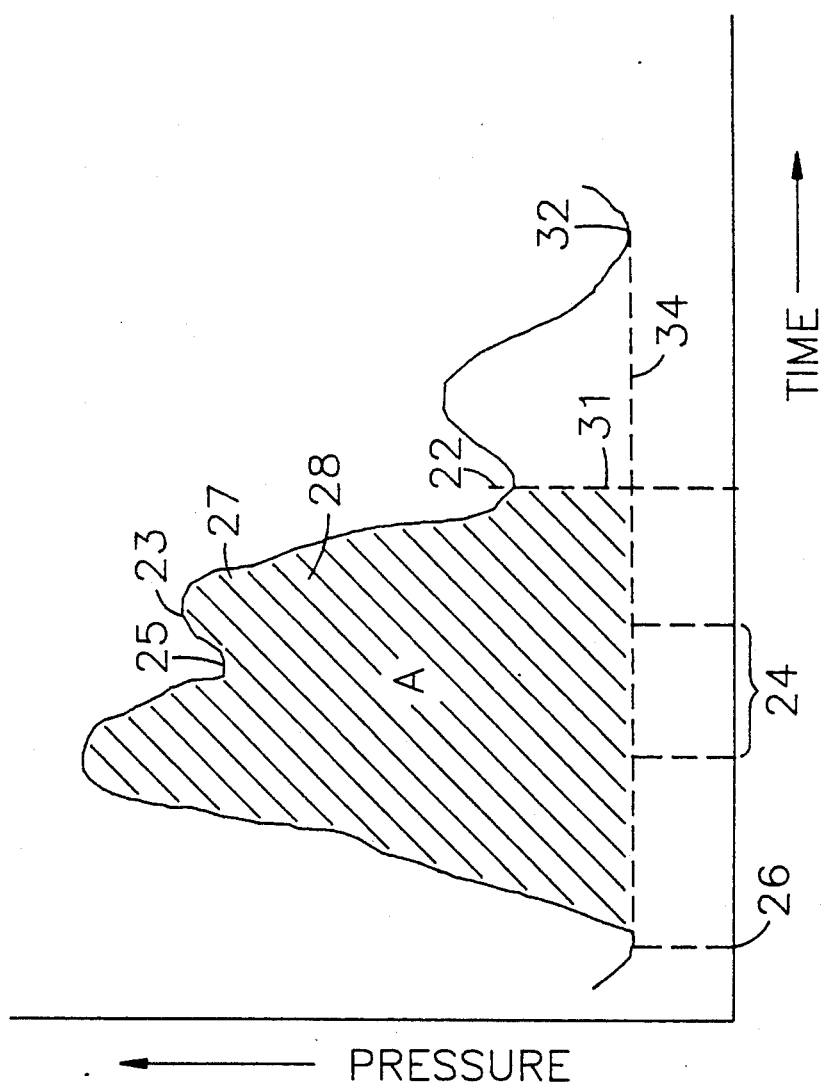
FIG. 5 is another special reflective curve showing Area A.
Figure 6:
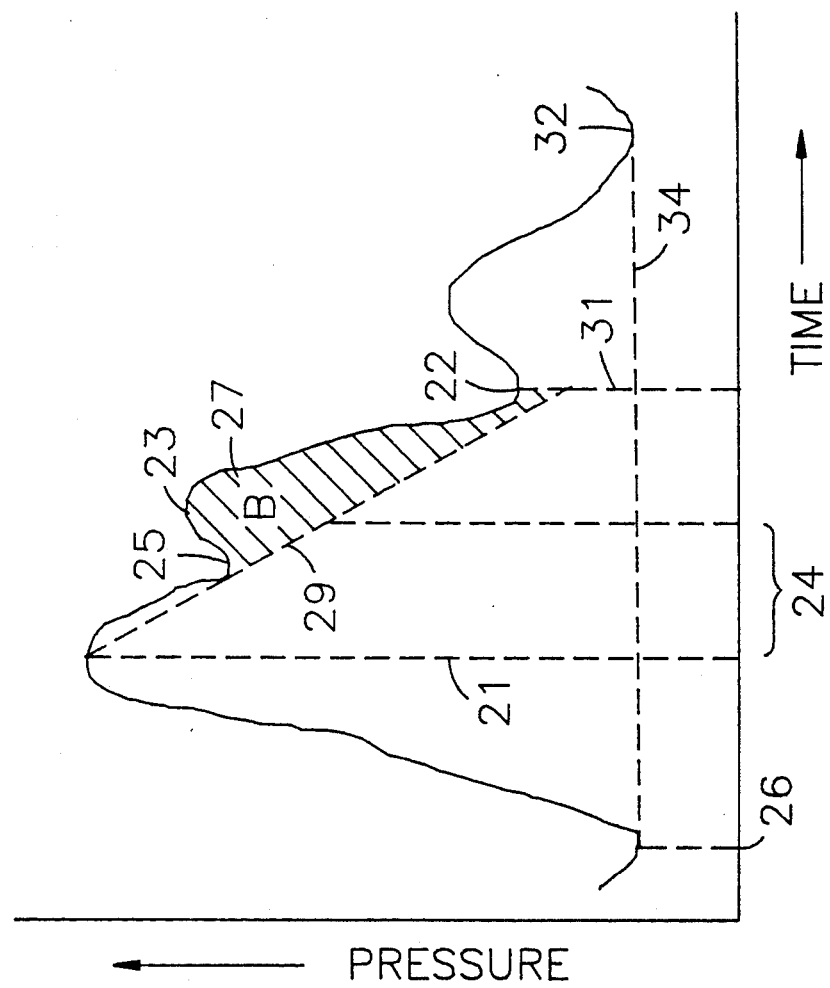
FIG. 6 is the same reflexive curve as FIGS. 5 and 6, showing Area B.

When a reflective wave is determined (FIG. 2), a line 29 is calculated from point 21 with a slope equal to the most negative slope between the time values, 38 and 31, of points 21 and 22, respectively, and a point on said line 31. The area 27 above line 29 is assigned as "Area B" and is subtracted from the area under the curve between the time of the beginning of the pulse 26 and the time value of the dicrotic notch 31 (Area A) for purposes of calculating SA. In curves such as illustrated in FIG. 4 where line 29 intersects a line 34 representing the diastolic pressure before it intersects line 31, an area 33 is defined as the area under the pulse pressure curve bounded by line 35 from apparent systolic peak 21 and point 36 where lines 34 and 31 intersect (FIG. 6 shows this area as Area B), and is substracted in determining corrected SA.

For any pulse which is reflective, the computer algorithm subtracts from or adds to said area A any portion, B, of said area A, representing an approximate area due to wave reflection to obtain a stroke area, SA; and the algorithm calculates CO as a product of SA and HR. In the preferred embodiment, the algorithm corrects the resultant CO by multiplying using an admittance factor, Y, which is a function of pulse pressure and mean pressure. A relationship between Y and CO/SA.HR is determined as a function by comparing the thermodilution derived CO's for each patient in the study population over a range of pulse pressures, means pressures, heart rates, and vascular impedances. Very accurate, reproducible CO's and CO trends can be obtained using a dynamic admittance expression, exceeding the accuracy and reproduceability of other pulse contour methods. The Y function is preferably programmed into the algorithm so that corrected CO information is continuously available for new subjects without the need to calibrate for any subject with thermodilution methods or any other invasive method. Said portion B is determined by a method which comprises continuously calculating for each pulse the portion of the area under the pulse contour curve from where grade of slope equals zero and then increases by a set amount, representing the beginning of a reflected wave, to a point on said curve where said grade of slope returns to zero, said point where said grade of slope returns to zero representing the dicrotic notch. The set amount is greater than −200 mm Hg-sec-1 and said point on said curve where said grade of slope returns to zero is greater than −60 mm Hg-sec-1.

The contribution reflective waves make to the stroke area changes depending on the location and position the data is recorded from. For example, the data from the radial artery of the wrist will differ from the data from the femoral artery of the groin.

When the pulse pressure wave is normal (FIG. 1) or damped (FIG. 3) no subtractions or additions are necessary.

As a preferred embodiment, an algorithm is presented below in Turbo C language showing the preferred constants, lookup tables, and the like.

```
double gen_gratzline(struct curve_data curvestuff, struct notch_data notchstuff,
          int the_gap, int *reverb, int *newpeak)
{
  int x1,x2,y1,y2;
  int minslope = 0;
  int testpoint;
  int i, data_point, extrapolation;
  double m, b, new_sum = 0;
  int firstval, temp;
   if (the_gap >= 60)
      *newpeak = peak_corrected(curvestuff,notchstuff);
   x1 = (curvestuff).top;
   y1 = buff_ptr[x1];
   for (i = x1; i <= notchstuff.start-5; i++)
   {  y2 = buff_ptr[i+1];
     m  = y2 - y1;
     y1 = y2;
     if (m < minslope)
        minslope = m;
  }
  x1 = curvestuff.top;
  y1 = buff_ptr[x1];
   x2 = (notchstuff).start;
   b = y1 - (m*x1);
    testpoint = (m*(notchstuff.start)) + b;
    if (testpoint < buff_ptr[curvestuff.start])
```

```
  {x2 = (notchstuff.start);
   y2 = buff_ptr[curvestuff.start];
   m  = (y2 - y1)/(x2 - x1);
   b  = y1 - (m*x1);
  }
   firstval = buff_ptr[curvestuff.start];
   for (i = curvestuff.start; i <= x1; ++i)
     new_sum = new_sum + buff_ptr[i] - firstval;
  *reverb = 0;
  for (i = x1+1; i <= x2; ++i)
  {
     data_point = buff_ptr[i];
     if (data_point > *newpeak)
     {
        *reverb = *reverb + (data_point - *newpeak);
        data_point = *newpeak;
     }
     extrapolation = (m*i) + b;
     if (extrapolation > data_point)
      {temp = data_point - firstval;
        if (temp < 0)
          temp = 0;
        new_sum = new_sum + temp;
      }
     else if (extrapolation > firstval)
       {new_sum = new_sum + extrapolation - firstval;
       }
  }
     return(new_sum);
}
 char is_reflection(struct curve_data curvestuff)
{
   int start = curvestuff.top,
       end   = start+10,
       i     = start,
       slope;
   char done = FALSE;
       while ((i < end) AND (!done))
     {
        slope = buff_ptr[i+2] - buff_ptr[i];
        if (slope >= 0)
          done = TRUE;
        i++;
     }
     return(done);
}
 int peak_corrected(struct curve_data curvestuff, struct notch_data notchstuff)
{
   #define spike -60
   int i,
       start = curvestuff.top,
       end;
   double temp;
    int slope,y1,y2;
    int threshold = buff_ptr[start];
   char done = FALSE;
     temp = notchstuff.start-5;
```

```
    temp = (start + temp)/2;
 end = temp;
  i = start+5;
  while (!done)
  {
     y1 = buff_ptr[i];
     y2 = buff_ptr[i+3];
     slope = y2 - y1;
     if (slope > spike)
     {
      done = TRUE;
       threshold = y1;
     }
      if (++i >=end)
      done = TRUE;
   }
   if (threshold < buff_ptr[start])
       {threshold = buff_ptr[i];
       }
       return(threshold);
}
  double get_startoffset(double period)
{
  double time_offset;
  double temp;
   if (period > 1.4)
      time_offset = (double) timeconst*(0.18);
  else if (period > 0.7)
      time_offset = (double) timeconst*(0.16);
  else if (period > 0.65)
      time_offset = (double) timeconst*(0.14);
  else if (period > 0.6)
      time_offset = (double) timeconst*(0.13);
  else if (period > 0.55)
      time_offset = (double) timeconst*(0.12);
  else if (period > 0.5)
      time_offset = (double) timeconst*(0.11);
  else if (period > 0.4)
      time_offset = (double) timeconst*(0.08);
     else if (period <= 0.015)
      time_offset = (double) timeconst*(0.015);
  else
  {
      temp = (period - 0.015)*(period - 0.015);
     temp = temp*temp;
     temp = temp*temp;
      time_offset = (double) timeconst*( 0.02 + (2.5*temp) );
  }
    return(time_offset);
}
 double get_Qoffset(double period)
{
  double Qoffset;
   if (period > 1.2)
     Qoffset = 0.45;
  else if (period > 1)
     Qoffset = 0.5;
```

```
    else if (period > 0.8)
       Qoffset = 0.58;
    else if (period > 0.7)
       Qoffset = 0.68;
    else if (period > 0.5)
       Qoffset = 0.75;
    else
       Qoffset = 0.95;
       return(Qoffset);
}
  void scan_notch(struct curve_data curvestuff,struct notch_data *notchstuff)
{
   int y1,y2,slope;
   int upcount = 0,
   downcount = 0;
   int notch_loc,
       notch_x;
   char done = FALSE;
   char done2 = FALSE;
    int critval = -5,
        crittimes = 1;
   int _x,tt = 0;
   int i;
   unsigned int start,end;
   double twave_offset = 0;
   double pulse_period, Qoffset;
      pulse_period = (double) (curvestuff.endx - curvestuff.start)/timeconst;
      twave_offset = get_startoffset(pulse_period);
   Qoffset    = get_Qoffset(pulse_period);
    start = curvestuff.top + twave_offset;
    end = (int) (curvestuff.start +
              (curvestuff.endx-curvestuff.start)*Qoffset);
    _x = curvestuff.top_x + twave_offset;
     y1 = buff_ptr[start];
   i = start;
    while ((i <= end) AND (!done))
{
     _x++;
     i++;
     if (_x >= 640)
       _x = 0;
     y2 = buff_ptr[i];
     slope = y2 - y1;
     y1 = y2;
      if (slope >= critval)
   {
      upcount++;
      if (upcount >= 2)
         downcount = 0;
   }
     else if (slope < critval)
   {
      downcount++;
      if (downcount >= 5)
         upcount = 0;
   };
      if (upcount >= crittimes)
```

```
    {
        notch_loc = i - (crittimes+1);
        notch_x = _x - (crittimes+1);
      done = TRUE;
    }
  }
  if (done == FALSE)
  {
        notch_loc = i - (crittimes+1);
        notch_x = _x - (crittimes+1);
      done = TRUE;
  }
  if (done)
  {
   (*notchstuff).start = notch_loc;
   (*notchstuff).x     = notch_x;
  }
  else
   (*notchstuff).start = 0;
  if (done)
  {
   while ((!done2) AND (i <= end))
   {
        slope = buff_ptr[i+2] - buff_ptr[i];
        if (slope > 0)
          done2 = TRUE;
        i++;
        tt++;
   }
   if (done2)
   {
        notch_loc = i;
        notch_x   = _x + tt;
   }
   (*notchstuff).start = notch_loc;
   (*notchstuff).x     = notch_x;
  }
 }
 void getarea(struct curve_data *curvestuff)
{
 int i;
   for  (i = (*curvestuff).start; i <= (*curvestuff).endx; i++)
      (*curvestuff).sum1 = (*curvestuff).sum1 + buff_ptr[i] - curvemin;
}
 double getnotch_area(struct curve_data curvestuff,struct notch_data notchstf)
{
 double tempsum = 0;
 double _temp;
 int baselength,i;
  int firstval,yval, temp;
 int xx;
  xx = curvestuff.x1;
   firstval   = buff_ptr[curvestuff.start];
   baselength = notchstf.start - curvestuff.start + 1;
  for (i = curvestuff.start; i <= notchstf.start; ++i)
  {
    if (xx >= 640)
     xx = 0;
```

```
        yval = buff_ptr[i];
        if (yval < firstval)
           yval = firstval;
        tempsum = (double) (tempsum + yval);
        xx++;
      }
      _temp = (double) baselength*firstval;
      tempsum = (double) (tempsum - _temp);
      return(tempsum);
}
double admittance(int mean_pressure, int pulse_pressure, int notch_gap)
{
  double Y;
    if (mean_pressure >= 100)
       { Y = 1.94 + (18.01*exp(-0.14*pulse_pressure));
    if (notch_gap <= 0)
        Y += Y*(0.5);
     else if (notch_gap <= 3)
        Y += Y*(0.3);
      if ((pulse_pressure >= 75) AND (pulse_pressure <= 79))
      { if (notch_gap < 10)
           notch_gap = 10;
         else if (notch_gap > 40)
           notch_gap = 40;
         Y = Y + (notch_gap - 25)*(0.0369);
      }
       else if ((pulse_pressure >= 50) AND (pulse_pressure <= 59))
      { if (notch_gap < -10)
           notch_gap = -10;
         else if (notch_gap > 25)
           notch_gap = 25;
         Y = Y - (notch_gap - 25)*(0.0355);
      }
       else if ((pulse_pressure > 140) OR (pulse_pressure < 40))
          if (alarm) printf("%c",7);
   } /* end MP >= 100 */
  else if (mean_pressure >= 95)
    { /*Y = 2.73 + (3.25)*exp(-0.035*pulse_pressure);*/
       Y = 0.04 + (5)*exp(-0.008*pulse_pressure);
    if (notch_gap <= 0)
        Y += Y*(0.5);
     else if (notch_gap <= 3)
        Y += Y*(0.3);
     if ((pulse_pressure > 90) OR (pulse_pressure < 45))
        if (alarm)  printf("%c",7);
   } /* end MP >= 95 */
  else if (mean_pressure >= 90)
    { Y = 1.4  + (16.8)*exp(-0.038*pulse_pressure);
    if (notch_gap <= 0)
        Y += Y*(0.5);
     else if (notch_gap <= 3)
        Y += Y*(0.3);
     if ((pulse_pressure > 120) OR (pulse_pressure < 40))
        if (alarm)  printf("%c",7);
   } /* end MP >= 90 */
  else if (mean_pressure >= 85)
    { Y = 0.12 + (4.3)*exp(-0.007*pulse_pressure);
```

```
        if (notch_gap <= 0)
            Y += Y*(0.5);
        else if (notch_gap <= 3)
            Y += Y*(0.3);
        if ((pulse_pressure > 90) OR (pulse_pressure < 40))
            if (alarm) printf("%c",7);
    } /* end MP >= 85 */
    else if (mean_pressure >= 80)
    { Y = 0.26 + (4.6)*exp(-0.009*pulse_pressure);
        if (notch_gap <= 0)
            Y += Y*(0.5);
        else if (notch_gap <= 3)
            Y += Y*(0.3);
        if ((pulse_pressure > 80) OR (pulse_pressure < 35))
            if (alarm) printf("%c",7);
    } /* end MP >= 80 */
    else if (mean_pressure >= 75)
    { Y = 2.50 + (10.97)*exp(-0.068*pulse_pressure);
        if (notch_gap <= 0)
            Y += Y*(0.5);
        else if (notch_gap <= 3)
            Y += Y*(0.3);
        if ((pulse_pressure >= 60) AND (pulse_pressure <= 64))
        { if (notch_gap > 25)
            notch_gap = 25;
          else if (notch_gap < 5)
            notch_gap = 5;
          Y = Y - (notch_gap - 20)*(0.1197);
        }
        else if ((pulse_pressure >= 70) AND (pulse_pressure <= 74))
        { if (notch_gap < 10)
            notch_gap = 10;
          else if (notch_gap > 20)
            notch_gap = 20;
          Y = Y - (notch_gap - 20)*(0.077);
        }
        else if ((pulse_pressure >= 50) AND (pulse_pressure <= 54))
        { if (notch_gap < 5)
            notch_gap = 5;
          else if (notch_gap > 25)
            notch_gap = 25;
          Y = Y - (notch_gap - 20)*(0.0752);
        }
        else if ((pulse_pressure > 85) OR (pulse_pressure < 30))
            if (alarm) printf("%c",7);
    } /* end MP >= 75 */
    else if (mean_pressure >= 70)
    { Y = 1.31 + (16.03)*exp(-0.05*pulse_pressure);
        if ((pulse_pressure >= 60) AND (pulse_pressure <= 64))
        { if (notch_gap > 20)
            notch_gap = 20;
          else if (notch_gap < 0)
            notch_gap = 0;
          Y = Y - (notch_gap - 20)*(0.136);
        }
        else if ((pulse_pressure >= 55) AND (pulse_pressure <= 59))
        { if (notch_gap > 20)
```

```
         notch_gap = 20;
      else if (notch_gap < 5)
         notch_gap = 5;
      Y = Y - (notch_gap - 20)*(0.1257);
   }
     else if ((pulse_pressure >= 80) AND (pulse_pressure <= 84))
   { if (notch_gap < 25)
        notch_gap = 25;
      else if (notch_gap > 30)
         notch_gap = 30;
      Y = Y + (notch_gap - 20)*(0.1257);
   }
     else if ((pulse_pressure > 85) OR (pulse_pressure < 30))
        if (alarm)  printf("%c",7);
   } /* end MP >= 70 */
else if (mean_pressure >= 65)
    { Y = 1.7 + (5.69)*exp(-0.028*pulse_pressure);
      if ((pulse_pressure >= 50) AND (pulse_pressure <= 54))
   { if (notch_gap < 5)
        notch_gap = 5;
      else if (notch_gap > 30)
         notch_gap = 30;
      Y = Y - (notch_gap - 20)*(0.0743);
   }
     else if ((pulse_pressure >= 40) AND (pulse_pressure <= 44))
   { if (notch_gap < 4)
        notch_gap = 4;
      else if (notch_gap > 15)
         notch_gap = 15;
      Y = Y - (notch_gap - 20)*(0.0821);
   }
     else if ((pulse_pressure > 70) OR (pulse_pressure < 20))
        if (alarm)  printf("%c",7);
   } /* end MP >= 65 */
else if (mean_pressure >= 60)
    { Y = 2.32 + (20.28)*exp(-0.066*pulse_pressure);
      if ((pulse_pressure >= 70) AND (pulse_pressure <= 79))
   { if (notch_gap < 15)
        notch_gap = 15;
      else if (notch_gap > 30)
         notch_gap = 30;
      Y = Y + (notch_gap - 20)*(0.0456);
   }
     else if ((pulse_pressure >= 45) AND (pulse_pressure <= 49))
   { if (notch_gap < 5)
        notch_gap = 5;
      else if (notch_gap > 25)
         notch_gap = 25;
      Y = Y - (notch_gap - 20)*(0.0784);
   }
     else if ((pulse_pressure >= 65) AND (pulse_pressure <= 69))
   { if (notch_gap < 14)
        notch_gap = 14;
      else if (notch_gap > 25)
         notch_gap = 25;
      Y = Y + (notch_gap - 20)*(0.0519);
```

```
    }
      else if ((pulse_pressure > 80) OR (pulse_pressure < 30))
         if (alarm)  printf("%c",7);
   } /* end MP >= 60 */
else
     { Y = 2.64 + (6.16)*exp(-0.056*pulse_pressure);
      if ((pulse_pressure > 70) OR (pulse_pressure < 15))
         if (alarm)  printf("%c",7);
   } /* end MP < 60 */
     return(Y);
}
   void do_calcs(struct curve_data curvestuff,struct notch_data notchstf,
                 double _adjust)
{
  double notcharea;
  double totalarea = curvestuff.sum1;
  int timeinterval = curvestuff.endx - curvestuff.start;

int frequency = (60*timeconst/timeinterval);
  double mean_pressure;
  double strokevolume,stroke;
 double notchgap,
         top_notchgap;
  double temp,Y_factor;
  int top_mark, gap, newpeak;
  int newgap, reverbs;
  double CO,CO2, resistance;
   int decaytemp;
   int sign2;
  char   reflects = FALSE;
  double decayslope;
  double Qpressure, avgQ;
  double gapdouble;
  int    mp, pp, ng;
    top_mark = curvestuff.top;
    sys = buff_ptr[top_mark];
    sys = (double) pressure*(sys - curvemin)/(curvemax - curvemin);
   top_mark = curvestuff.start;
    dia = buff_ptr[top_mark];
     dia = (double) pressure*(dia - curvemin)/(curvemax - curvemin);
   gap = sys - dia;
    notchgap = buff_ptr[notchstf.start];
    top_notchgap = buff_ptr[curvestuff.top];
  notchgap = pressure*
             (notchgap - buff_ptr[curvestuff.start])/(curvemax-curvemin);
   top_notchgap = pressure*
             (top_notchgap - buff_ptr[notchstf.start])/(curvemax-curvemin);
    notcharea = getnotch_area(curvestuff,notchstf);
    newpeak = buff_ptr[curvestuff.top];
    strokevolume=gen_gratzline(curvestuff,notchstf,gap,&reverbs,&newpeak);
    mean_pressure = totalarea/(timeinterval*_adjust);
    if (newpeak == buff_ptr[curvestuff.top])
   newgap = gap;
  else
  {
      temp = (double) pressure*(newpeak-curvemin)/(curvemax-curvemin);
```

```
   temp = temp - dia;
      newgap = temp + ((0.5)*(gap-temp));
}
avgNG = avgNG + notchgap;
   reflects = is_reflection(curvestuff);
   if ( ((notchgap <= 13) OR (gap < 60)) AND (!reflects))
{
   strokevolume = notcharea;
}
else if (sys < 140)
{
   strokevolume = (strokevolume + reverbs);
}
else
{
   strokevolume = (strokevolume);
   gapdouble = gap;
      newgap = temp + ((0.75)*(gapdouble-temp));
}
   mp = (int) mean_pressure;
 ng = (int) notchgap;
pp = gap;
 Y_factor = admittance(mp, pp, ng);
   stroke = strokevolume;
   stroke = stroke*Y_factor/(_adjust*timeconst);
   CO = BSA*stroke*frequency;
} /* end procedure do_calculations */
```

Various alternatives, modifications, and improvements should become readily apparent to those skilled in the art reading the above specification without departing from the spirit and scope of the invention as set forth in the following claims.

We claim:

1. A method for continuously determining cardiac output (CO) in a subject comprising:

providing a non-invasive sensor device for continuously measuring arterial blood pressure in a subject;

continuously measuring arterial blood pressure and obtaining arterial blood pressure data with said device;

continuously converting said arterial blood pressure data to a digital signal representative of a pulse contour curve waveform;

continuously calculating heart rate (HR), grade of slope, systolic peak pressure, the presence of reflected waves, and pressure at the dicrotic notch from said digital signal;

determining the area, A, under said pulse contour curve from the start of a pulse to the dicrotic notch of said pulse contour curve;

for any pulse which is reflective, subtracting from said area A any portion, B, of said area A, representing an approximate area due to wave reflection to obtain a stroke area, SA; and calculating CO as a product of SA and HR.

2. Method in accordance with claim 1 further comprising correcting the resultant CO by multiplying using an admittance factor, Y, which is a function of pulse pressure, said function having been previously determined statistically over a patient population by comparison of the product of SA and HR for a particular patient with thermodilution cardiac output data over a range of pulse pressures for said patient.

3. Method in accordance with claim 2 wherein said step of correcting CO comprises using a standard Y curve for every subject.

4. Method in accordance with claim 2, further including determining said admittance factor, Y, for a particular site of measurement of arterial blood pressure in each of the patients in said patient population.

5. Method in accordance with claim 1 further including determining said portion B by a method which comprises continuously calculating for each pulse the portion of the area under the pulse contour curve from where grade of slope equals zero and then increases by a set amount, representing the beginning of a reflected wave, to a point on said curve where said grade of slope returns to zero, said point where said grade of slope returns to zero representing the dicrotic notch.

6. Method in accordance with claim 5 wherein said set amount is greater than −200 mm Hg-sec-1 and said point on said curve where said grade of slope returns to zero is greater than −60 mm Hg-sec-1.

7. Method in accordance with claim 5 further including determining said set amount by a formula based on the pulse pressure of the previous pulse.

8. Method in accordance with claim 5 further including determining a corrected value representing the true systolic peak for each pulse which contains a reflected wave and a resultant elevated, false systolic peak, and an extrapolation line from said true systolic peak and the dicrotic notch is calculated, said extrapolation line marking a lower boundary of said area, B, said area B having an upper boundary marked by said pulse contour curve including said elevated, false systolic peak.

9. Method in accordance with claim 8 further including determining an additional area, C, defined as the area above the true systolic peak, and subtracting said additional area C from said area A.

10. Method in accordance with claim 8 wherein said area B is bound on one side by the false systolic peak and on the opposite side by a point on said pulse contour curve for said pulse where the time ordinate equals that of the dicrotic notch or the pressure is the diastolic pressure.

11. Method in accordance with claim 1 wherein said site is an index finger using a device which measures variation in blood pressure at said site.

12. Method in accordance with claim 11, further including calculating said Y according to a formula $$A + B \cdot e - (K(mp) \cdot pp)$$

where A is a function of mean pressure, B is a function of mean pressure, K is a function of mean pressure, mp represents mean pressure, and pp represents pulse pressure.

13. Method in accordance with claim 1 further comprising continuously calculating diastolic pressure, pulse pressure, mean pressure, and diastolic area.

14. Apparatus for continuously determining cardiac output (CO) in a subject comprising:
   non-invasive sensor means for continuously measuring arterial blood pressure data at a site on said subject;
   means for continuously converting said arterial blood pressure data to a digital signal representative of a pulse contour curve waveform;
   means for continuously calculating heart rate (HR), grade of slope, systolic peak pressure, the presence of reflected waves, and pressure at the dicrotic notch from said digital signal;
   means for determining the area, A, under said pulse contour curve from the start of a pulse to the dicrotic notch of said pulse contour curve;
   means for subtracting from said area A any portion, B, of said area A, representing an approximate area due to wave reflection to obtain a stroke area, SA; and
   means for calculating CO as a product of SA and HR.

15. Apparatus according to claim 14 further comprising means for correcting the resultant CO by multiplying using an admittance factor, Y, which is a function of pulse pressure, said function having been previously determined statistically over a patient population by comparison of the product of SA and HR for a particular patient with thermodilution cardiac output data over a range of pulse pressures for said patient.

16. Apparatus according to claim 14 which comprises means for continuously calculating for each pulse the portion of the area under the pulse contour curve from where grade of slope equals zero and then increases by a set amount, representing the beginning of a reflected wave, to a point on said curve where said grade of slope exceeds −60 mm Hg-sec-1, said point where said grade of slope exceeds −60 mm Hg-sec-1 representing the dicrotic notch.

17. Apparatus according to claim 14 wherein said means for continuously measuring arterial blood pressure data at a site on said subject comprises means for continuously measuring variation in pressure at an finger or toe site and means for continuously converting the resultant analogue data to digital data representing pulse pressure.

18. A method for continuously determining cardiac output in a subject comprising:
   providing a minimally invasive sensor device for continuously measuring arterial blood pressure in a subject:
   continuously measuring arterial blood pressure and obtaining arterial blood pressure data with said device;
   continuously converting said arterial blood pressure data to a digital signal representative of a pulse contour curve waveform;
   continuously calculating heart rate (HR), grade of slope, systolic peak pressure, the presence of reflected waves, and pressure at the dicrotic notch from said signal;
   determining the area, A, under said pulse contour curve from the start of a pulse to the dicrotic notch of said pulse contour curve;
   for any pulse which is reflective, subtracting from said area A any portion, B, of said area A, representing an approximate area due to wave reflection to obtain a stroke area, SA;
   and calculating CO as a product of SA and HR.

19. Method in accordance with claim 18 wherein said site is a radialartery and further including measuring said arterial blood pressure at said site by means of a minimally invasive catheter.

20. Apparatus for continuously determining cardiac output (CO) in a subject comprising:
   minimally invasive sensor means for continuously measuring arterial blood pressure data at a site on said subject;
   means for continuously converting said arterial blood pressure data to a digital signal representative of a pulse contour curve waveform;
   means for continuously calculating heart rate (HR), grade of slope, systolic peak pressure, the presence of reflected waves, and pressure at the dicrotic notch from said signal;
   means for determining the area, A, under said pulse contour curve from the start of a pulse to the dicrotic notch of said pulse contour curve;
   means for subtracting from said area A any portion, B, of said area A, representing an approximate area due to wave reflection to obtain a stroke area, SA;
   and means for calculating CO as a product of SA and HR.

21. Apparatus according to claim 20 wherein said means for continuously measuring arterial blood pressure data at a site on said subject comprises catheter means for continuously measuring pulse pressure data at a radialartery.

* * * * *